US012806316B2

(12) United States Patent
Kang et al.

(10) Patent No.: US 12,806,316 B2
(45) Date of Patent: Nov. 24, 2026

(54) HIGHLY CONDUCTIVE TISSUE-LIKE HYDROGEL ADHESIVE FOR BIOELECTRONICS AND MANUFACTURING THEREOF

(71) Applicant: KOREA ADVANCED INSTITUTE OF SCIENCE AND TECHNOLOGY, Daejeon (KR)

(72) Inventors: Jiheong Kang, Daejeon (KR); Jooyeun Chong, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 138 days.

(21) Appl. No.: 18/626,529

(22) Filed: Apr. 4, 2024

(65) Prior Publication Data

US 2025/0152786 A1 May 15, 2025

(30) Foreign Application Priority Data

Nov. 10, 2023 (KR) ........................ 10-2023-0155264

(51) Int. Cl.

| | |
|---|---|
| ***A61L 31/04*** | (2006.01) |
| ***A61B 5/259*** | (2021.01) |
| ***A61B 5/268*** | (2021.01) |
| ***A61L 31/14*** | (2006.01) |
| ***C09J 9/00*** | (2006.01) |
| ***C09J 9/02*** | (2006.01) |
| *C09J 133/02* | (2006.01) |

(52) U.S. Cl.

CPC ............ *A61L 31/041* (2013.01); *A61B 5/259* (2021.01); *A61B 5/268* (2021.01); *A61L 31/14* (2013.01); *A61L 31/145* (2013.01); *C09J 9/00* (2013.01); *C09J 9/02* (2013.01); *C09J 133/02* (2013.01)

(58) Field of Classification Search

None

See application file for complete search history.

(56) References Cited

U.S. PATENT DOCUMENTS

2019/0390068 A1* 12/2019 Feig ........................ A61L 27/16
2020/0291274 A1* 9/2020 Iwase .................. A61N 1/0492

OTHER PUBLICATIONS

Jooyeun Chong et al., "Adhesive-free hydrogel bioelectronics enabled by a template-directed assembly of PEDOT:PSS", 2023 MRS Spring meeting & Exhibit, Apr. 13, 2023, San Francisco, Califomia, total 17 pages.

Jooyeun Chong et al., "Highly conductive tissue-like hydrogel interface through template-directed assembly", Nature Communications (2023) 14: 2206, Apr. 18, 2023, total 12 pages.

(Continued)

*Primary Examiner* — Chinessa T. Golden

(74) *Attorney, Agent, or Firm* — LEX IP MEISTER, PLLC

(57) ABSTRACT

The present invention relates to a highly conductive tissue-like hydrogel adhesive that provides a hydrogel having three-dimensional nanofibers including a double network in which a soft and stretchable polyacrylic acid network and a conductive PEDOT:PSS network are uniformly formed along the polyacrylic acid network, thereby exhibiting excellent adhesive properties, as well as physical properties similar to living tissue, high stretchability, and high electrical properties, and a manufacturing method thereof.

11 Claims, 22 Drawing Sheets
(2 of 22 Drawing Sheet(s) Filed in Color)

(56) References Cited

OTHER PUBLICATIONS

Gang Li et al., "Highly Conducting and Stretchable Double-Network Hydrogel for Soft Bioelectronics", Advanced Materials 34.15 (2022): 2200261, Feb. 2022, total 10 pages.
Vivian R. Feig et al., "Mechanically tunable conductive interpenetrating network hydrogels that mimic the elastic moduli of biological tissue", Nature Communications 9.1 (2018): 2740, Jul. 2018, total 9 pages.
Baoyang Lu et al., "Pure PEDOT:PSS hydrogels", Nature Communications 10.1 (2019): 1043, Mar. 2019, total 10 pages.
Jue Deng et al., "Electrical bicadhesive interface for bioelectronics", Nature Materials 20.2 (2021): 229-236, Feb. 2021.
Tao Zhou et al., "3D printable high-performance conducting polymer hydrogel for all-hydrogel bioelectronic interfaces", Nature Materials vol. 22, Jun. 2023, 895-902.

* cited by examiner

【FIG. 3】
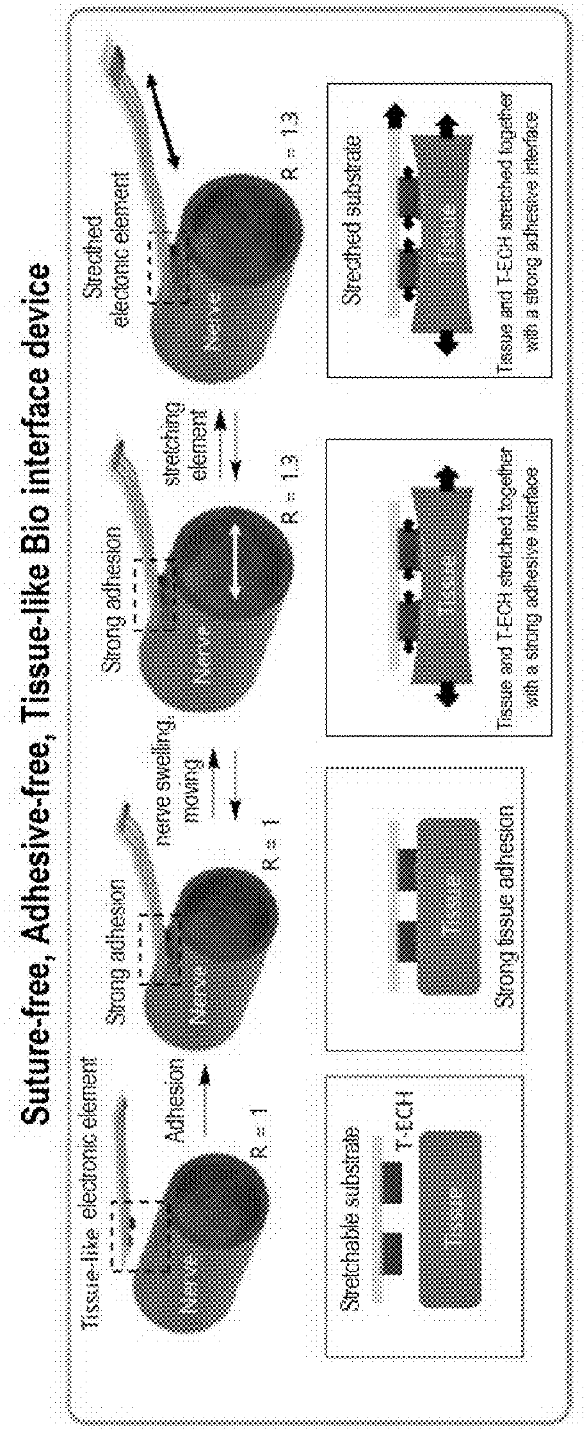

HIGHLY CONDUCTIVE TISSUE-LIKE HYDROGEL ADHESIVE FOR BIOELECTRONICS AND MANUFACTURING THEREOF

CROSS-REFERENCE TO RELATED APPLICATION(S)

This application claims the benefit of Korean Patent Application No. 10-2023-0155264 filed on Nov. 10, 2023 in the Korean Intellectual Property Office, the disclosure of which is incorporated herein by reference in its entirety.

TECHNICAL FIELD

The present invention relates to a highly conductive tissue-like hydrogel adhesive for bioelectronics having high conductivity and excellent stretchable property and adhesive property, and a manufacturing method thereof.

BACKGROUND

Bioelectronic interface devices have received considerable attention due to their importance in neuroscience, diagnostics, therapy, and wearable and implantable devices. However, the tissue interface electrodes used in most bioelectronic devices are still rigid and dry, which causes side effects such as inflammatory responses at the tissue interface.

Therefore, conductive hydrogels, which have tissue-like soft and well-stretchable mechanical properties, high water content, and excellent biocompatibility, have been considered as a promising material for tissue-interfacing electrodes. Among them, research on conductive hydrogels using conductive polymers with excellent biocompatibility has been actively conducted. The most representatively used conductive polymer is PEDOT:PSS, which has the advantages of high electrical conductivity and aqueous solution process ability.

However, conductive hydrogels that have developed in the past have mechanical properties similar to tissue, and have a drawback that they are low in electrical conductivity if well-stretched, and are easily broken, and not stretched when being high in electrical conductivity, namely, they have the conflict between the mechanical properties and the electrical properties.

That is, methods for synthesizing conductive hydrogels using conductive polymers including PEDOT:PSS are broadly divided into two types (FIGS. 1*a* and 1*b*).

The first method is to strengthen the PEDOT network responsible for electrical conductivity to make a hydrogel having high electrical conductivity (~40 S/cm) (FIG. 1*a*). However, in this case, crystalline PEDOT domains are formed, showing a high elastic modulus (~1 MPa) and low stretchability (~20%).

The second method is to insert PEDOT:PSS into a soft and stretchable polymer hydrogel network to achieve mechanical strength and high stretchability similar to biological tissue (FIG. 1*b*). However, this method shows low electrical properties (<1 S/cm) because the PEDOT network is poorly formed. Therefore, the need for a hydrogel that has both high electrical properties and physical properties similar to living tissues as a more effective biological tissue interface electrode material has emerged.

In addition, bioelectronic interface devices require good adhesion with tissue interfaces in order to transmit and receive stable electrical signaling to and from the body. However, the tissue adhesives reported so far have limitations in that they have poor electrical properties, require high voltage to operate, or have a low signal-to-noise ratio. Therefore, due to the absence of a hydrogel that has good electrical properties, mechanical properties, and adhesive properties (i.e., bonding properties), biological tissue devices have problems such as obtaining low-quality biological signals or requiring high operating voltage.

DETAILED DESCRIPTION OF THE INVENTION

Technical Problem

It is an object of the present invention to provide a tissue-like hydrogel that not only has excellent electrical properties and good stretchability when used as a tissue adhesive, but also is highly compatible as a material for bioelectronics that can ensure improved mechanical properties and adhesive properties with tissue interfaces.

It is another object of the present invention to provide a method of manufacturing a tissue-like hydrogel adhesive having high conductivity and excellent stretchable property and adhesive property.

Technical Solution

According to one embodiment of the present invention, there is provided a highly conductive tissue-like hydrogel adhesive in which:

a three-dimensional nanofiber containing a PEDOT network and a PSS network are formed along polyacrylic acid within a matrix containing polyacrylic acid, the three-dimensional nanofiber is formed by heating a hydrogel formed through polymerization of an acrylic acid monomer containing an organic solvent and PEDOT:PSS, which is a conductive polymer, so that PEDOT and PSS are separated and dispersed from the conductive polymer, and 4.8 to 9.1 parts by weight of the conductive polymer in the hydrogel is crosslinked with respect to 100 parts by weight of polyacrylic acid.

According to another embodiment of the present invention, there is provided a method of manufacturing a highly conductive tissue-like hydrogel adhesive, the method comprising:

a first step of adding an acrylic acid monomer, a polymerization initiator, and a crosslinking agent to a water-soluble solvent to prepare an acrylic acid monomer composition;

a second step of adding PEDOT:PSS as a conductive polymer to the acrylic acid monomer composition and thermally polymerizing the acrylic acid monomer to produce a hydrogel that formed a network containing polyacrylic acid as a matrix polymer; and a third step of heating the hydrogel that formed a network containing polyacrylic acid in an organic solvent to blow off all the solvent, thereby manufacturing a film containing three-dimensional nanofibers in which conductive polymers are formed uniformly and thinly along polyacrylic acid, which is a matrix polymer, wherein the conductive polymer in the third step separates PEDOT and PSS along a network containing polyacrylic acid to form a network, respectively, and wherein the conductive polymer is contained in an amount of 4.8 to 9.1 parts by weight with respect to 100 parts by weight of the acrylic acid monomer.

Advantageous Effects

According to the present invention, polyacrylic acid acts as a template polymer within a matrix containing polyacrylic acid by using soft polyacrylic acid and PEDOT:PSS as a conductive polymer together, so that the conductive polymers are connected to each other under heating of an organic solvent, and PEDOT and PEDOT form a three-dimensional structure of thin nanofibers along the polyacrylic acid, whereby a tissue-like hydrogel adhesive that has both high conductivity suitable for bioelectronics and physical properties similar to biological tissue and a method of manufacturing the same can be provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 briefly illustrates the operation principle of the highly conductive tissue-like hydrogel adhesive according to one embodiment of the invention.

DETAILED DESCRIPTION OF THE EMBODIMENTS

Through the specification, unless explicitly described to the contrary, the word "comprise" and variations such as "comprises" or "comprising" will be understood to imply the inclusion of stated elements but not the exclusion of any other elements. Through the specification, the terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party. Throughout the specification, the term "step of" does not mean "step for".

The terminology used herein is for the purpose of describing particular embodiments only and is not intended to be limiting of the invention, unless the context clearly indicates otherwise.

Exemplary embodiments of the present invention will be described in detail with reference to the above definitions and the accompanying drawings. However, these are presented as examples, and the invention is not limited thereby, and the invention is only defined by the scope of the claims described below.

A highly conductive tissue-like hydrogel adhesive and a manufacturing method thereof according to one embodiment of the present invention will be described in detail.

According to one embodiment of the present invention, there is provided a highly conductive tissue-like hydrogel adhesive in which:

a three-dimensional nanofiber containing a PEDOT network and a PSS network are formed along polyacrylic acid within a matrix containing polyacrylic acid, the three-dimensional nanofiber is formed by heating a hydrogel formed through polymerization of an acrylic acid monomer containing an organic solvent and PEDOT:PSS, which is a conductive polymer, so that PEDOT and PSS are separated and dispersed from the conductive polymer, and 4.8 to 9.1 parts by weight of the conductive polymer in the hydrogel is crosslinked with respect to 100 parts by weight of polyacrylic acid.

The present inventors have developed a method to uniformly connect PEDOT:PSS networks within a soft and highly stretchable polyacrylic acid hydrogel network, and confirmed through experiments that it simultaneously ensures excellent stretchable properties and mechanical properties, and also exhibits high conductivity and excellent adhesion to living tissue, thereby completing the present invention.

Therefore, the highly conductive tissue-like hydrogel adhesive of the present invention has more excellent physical properties than a conventional one and has no side effects such as inflammatory responses when applied to living tissue, and thus can be usefully used in bioelectronic interface devices.

Hereinafter, the highly conductive hydrogel of the present invention will be described with reference to the drawings.

Figure 1A:
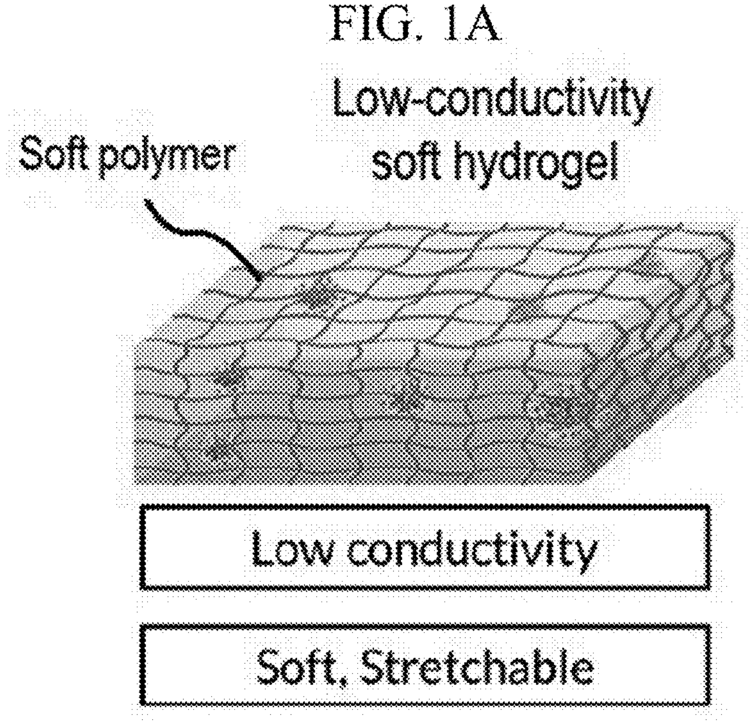
FIGS. 1*a* and 1*b* briefly illustrates the configuration of a conventional conductive hydrogel.
Figure 1B:
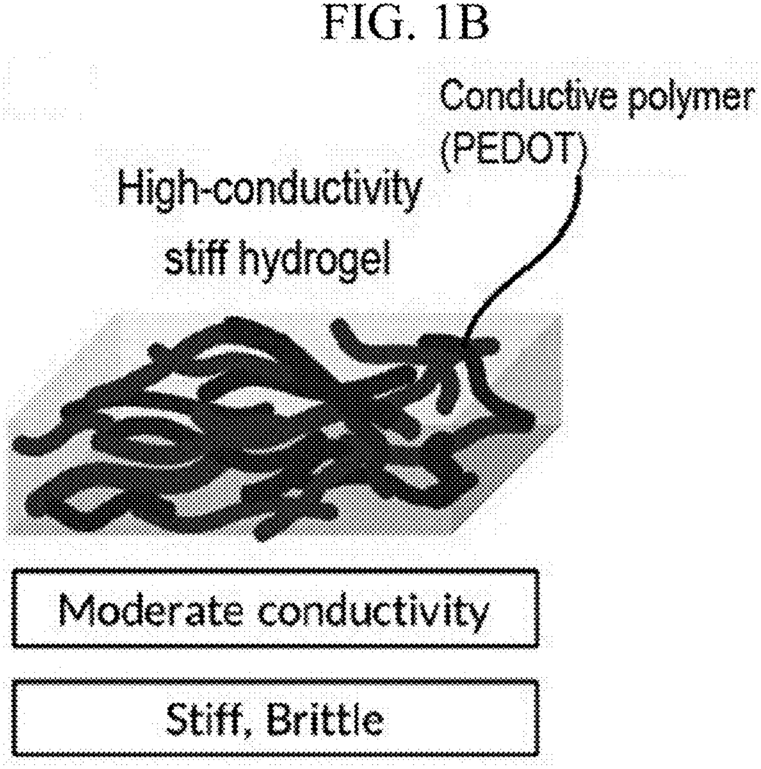
Figure 2A:
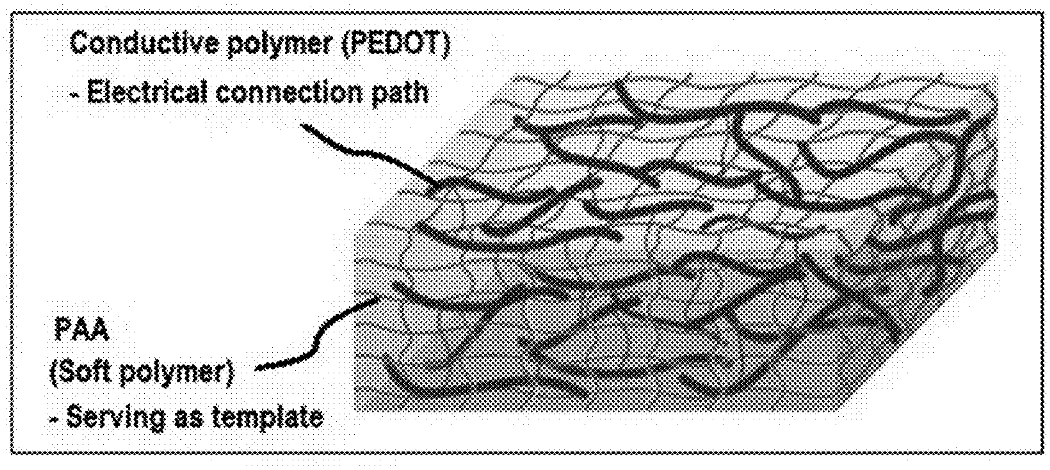
FIGS. 2*a* and 2*b* briefly illustrates the structure of a highly conductive tissue-like hydrogel adhesive according to an embodiment of the invention.
Figure 2B:
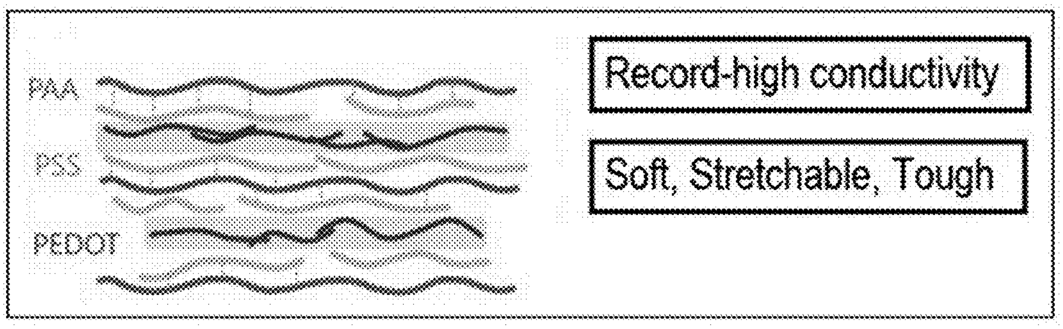

FIGS. 2*a* and 2*b* briefly illustrates the structure of a highly conductive tissue-like hydrogel adhesive according to an embodiment of the invention.

Although hydrogels that have been reported so far have smooth characteristics, they have a problem in that electrical connections are not activated and electrical properties are degraded. In addition, existing hydrogels with excellent electrical properties have very stiff physical properties, which limits their application fields.

Moreover, in order to ensure that existing conductive hydrogels exhibit high conductivity, the conductive material had to form large crystals throughout the entire matrix. Therefore, as it becomes more crystalline, its mechanical properties have no choice but to become stiffer.

Therefore, in the present invention, in order to solve such problems, a template network was made using poly(acrylic acid) (PAA), which is a hydrogel that is soft and has a strong bond with PEDOT:PSS, thereby imparting soft mechanical properties and making the electrical connection path of PEDOT uniform. Therefore, in the present invention, a double network hydrogel with a soft polymer network and a uniform conductive PEDOT:PSS network was prepared, thereby making it possible to create a tissue interface electrode that simultaneously has physical properties similar to tissues that did not exist in the past, high stretchability, and high electrical properties. That is, the present invention can provide a hydrogel that has soft properties and activated electrical connection paths.

The structure of the hydrogel (electrically conductive hydrogel through template-directed assembly; referred to as T-ECH) according to the present invention is shown in FIGS. 2*a* and 2*b*.

As shown in FIGS. 2*a* and 2*b*, the hydrogel of one embodiment of the invention is a double-structured hydrogel containing a soft polymer PAA network and a PEDOT:PSS network, which is a conductive polymer.

The hydrogel of one embodiment of the invention is formed with a three-dimensional nanofiber containing a PEDOT network and a PSS network along polyacrylic acid within a matrix containing polyacrylic acid.

In the hydrogel, the soft and highly stretchable polymer is a network containing polyacrylic acid (hereinafter PAA). In addition, the PEDOT:PSS network may refer to a three-dimensional conductive nanofiber in which PEDOT and PSS are separated from PEDOT:PSS, which is a conductive polymer, within polyacrylic acid, and each forms a network along the polyacrylic acid Specifically, the three-dimensional nanofiber is formed by heating a hydrogel formed through polymerization of an acrylic acid monomer containing an organic solvent and PEDOT:PSS, which is a conductive polymer, so that PEDOT and PSS are separated and dispersed from the conductive polymer.

Therefore, the step of adding the hydrogel having a network containing polyacrylic acid to a highly polar organic solvent such as DMSO and heating it to completely remove the solvent is performed. Accordingly, the final hydrogel of the present invention may include a three-dimensional conductive nanofiber in which PEDOT and PSS are separated from PEDOT:PSS contained in the hydrogel, and the conductive polymer is formed uniformly and thinly along polyacrylic acid, which is a matrix polymer (FIG. 2*b*).

In FIGS. 2*a* and 2*b*, PAA serves as a template during hydrogel formation, and can be included as a first network.

Further, a configuration including tertiary nanofibers in which PEDOT and PSS are separated to form a network may be included as a second network.

In the hydrogel, a very thin PEDOT network with metal-like conductivity formed uniformly and thinly in the hydrogel including the PAA network which is a highly stretchable polymer. This can be made by using PAA as a highly stretchable and soft first network, leading the way to create a PEDOT network.

Therefore, the hydrogel grows thinly along the PAA where PEDOT is the first network, and has very high conductivity.

More specifically, while the PAA is crosslinked with PEDOT:PSS used as a conductive polymer, the PAA forms a strong hydrogen bond with a PSS domain, thereby causing the PEDOT:PSS network to grow along the PAA's own network. Therefore, the electrically conductive PEDOT network is uniformly connected, so that hydrogel has high electrical conductivity. In addition, PEDOT:PSS is formed very uniformly within the matrix polymer PAA, so that all large-sized PEDOT:PSS lumps can be removed and therefore do not disturb the connection of PEDOT when hole conduction occurs in PEDOT. Therefore, the hydrogel of the present invention can achieve very high electrical conductivity of 200 S/cm or more, or 200 to 247 S/cm.

In addition, among the conductive polymers, PSS acts as a domain. However, as the PEDOT:PSS network is formed into thin fibers along the polyacrylic acid within the PAA nanonetwork through the manufacturing process described later, large-sized PSS domains are not formed. Thereby, all large-sized domains are removed from PEDOT:PSS, so that thin PEDOT:PSS fibers are connected to each other. Further, PEDOT connections are formed very uniformly along the PAA network, so that it does not disturb the PEDOT connections when hole conduction occurs in the PEDOT.

That is, conventionally, the PSS domains created by large PEDOT:PSS lumps during hydrogel production disturbed the connections between PEDOTs, thereby reducing electrical conduction. However, in the present invention, it is possible to suppress excessive growth of PSS as in the prior art, thereby preventing a decrease in electrical conductivity of the hydrogel.

Further, in order for hydrogels to easily sense biological signals and effectively provide biological stimulation, the biological tissue and the device must be strongly adhered, and not fall off even when an external force is applied.

The hydrogel of the present invention is made of PAA which can form a strong hydrogen bond with the skin, and also has a double structure, so that it has excellent energy dissipation ability and exhibits strong adhesion to the skin.

FIG. 3 briefly illustrates the operation principle of the highly conductive tissue-like hydrogel adhesive according to one embodiment of the invention.

As shown in FIG. 3, the present invention provides strong adhesion to tissue and can realize an ideal biological tissue device. Further, it is possible to realize a bio signal reading device with a very high signal-to-noise ratio using an electrode containing the hydrogel, and an electrical stimulation device that operates at a very low voltage.

In addition, the hydrogel of the present invention has excellent mechanical properties such as toughness and modulus, and also has strong properties against compression.

Therefore, the hydrogel can simultaneously have high electrical conductivity of 200 S/cm or more, good stretchability of 500% or more, 600% or more (preferably 600%), and soft physical properties having a modulus of 100 kPa or less.

According to one embodiment, the hydrogel may have an electrical conductivity of 200 S/cm or more, a maximum stretching rate of 400 to 600%, an impedance of 28Ω at 1 kHz, a tensile strength of 120 to 350 kPa, and a resistance storage capacity of 31 to 80 mC/cm2.

Further, the hydrogel may have a resistance change of 1.6 to 13% at 100% strain.

Preferably, the electrical conductivity of the hydrogel may be 200 S/cm or more, or 200 to 350 S/cm, or 230 to 350 S/cm.

The hydrogel may have a modulus of 100 kPa or less, or 10 to 90 kPa, or 10 to 50 kPa, or 10 to 30 kPa, or 30 kPa.

At this time, 4.8 to 9.1 parts by weight of the conductive polymer may be crosslinked with respect to 100 parts by weight of polyacrylic acid. If the content of the conductive polymer is less than 4.8 parts by weight, there is a problem that the electrical conductivity is low. If the content exceeds 9.1 parts by weight, there is a problem that the physical properties become stiff.

The polyacrylic acid may have a weight average molecular weight of 100,000 to 150,000 g/mol.

The hydrogel may further contain moisture to maintain its state. Since the content of the water-soluble solvent is intended to maintain the hydrogel state, the content thereof is not greatly limited.

Meanwhile, according to another embodiment of the invention, there can be provided a method of manufacturing a highly conductive tissue-like hydrogel adhesive, the method comprising: a first step of adding an acrylic acid monomer, a polymerization initiator, and a crosslinking agent to a water-soluble solvent to prepare an acrylic acid monomer composition; a second step of adding PEDOT:PSS as a conductive polymer to the acrylic acid monomer composition and thermally polymerizing the acrylic acid monomer to produce a hydrogel that formed a network containing polyacrylic acid as a matrix polymer; and a third step of heating the hydrogel that formed a network containing polyacrylic acid in an organic solvent to blow off all the solvent, thereby manufacturing a film containing three-dimensional nanofibers in which conductive polymers are formed uniformly and thinly along polyacrylic acid, which is a matrix polymer, wherein the conductive polymer in the third step separates PEDOT and PSS along a network containing polyacrylic acid to form a network, respectively, and wherein the conductive polymer is contained in an amount of 4.8 to 9.1 parts by weight with respect to 100 parts by weight of the acrylic acid monomer.

Figure 4:
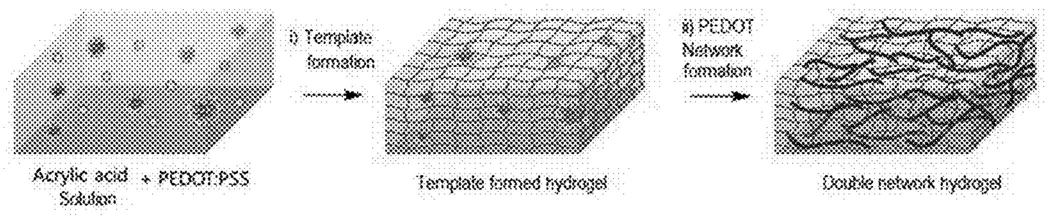
FIG. 4 briefly illustrates the manufacturing process of a highly conductive tissue-like hydrogel adhesive according to an embodiment of the invention.

FIG. 4 briefly illustrates the manufacturing process of a highly conductive tissue-like hydrogel adhesive according to an embodiment of the invention.

The hydrogel is produced by a method in which PAA, which is a soft polymer that strongly binds to PEDOT:PSS, acts as a template to induce connection of PEDOT. The synthesis method of the above hydrogel is shown in FIG. 4.

The first step is a step of preparing an acrylic monomer composition for forming PAA which is a soft polymer.

In the first step, the acrylic acid monomer composition may include 0.95 to 2 parts by weight of a polymerization initiator and 0.75 to 1.5 parts by weight of a crosslinking agent based on 100 parts by weight of acrylic acid monomer.

The conductive polymer is contained in an amount of 4.8 to 9.1 parts by weight with respect to 100 parts by weight of the acrylic acid monomer. If the content of the conductive polymer is less than 4.8 parts by weight, there is a problem that the electrical conductivity is low, and if the content exceeds 9.1 parts by weight, there is a problem that the physical properties become stiff.

The polymerization initiator may be one or more selected from the group consisting of ammonium persulfate, potassium persulfate, and sodium persulfate.

The crosslinking agent may be one or more selected from the group consisting of N,N-methylenebisacrylamide, polyethylene glycol diacrylate, and tetraethylene glycol diacrylate.

The second step is a step of mixing the acrylic acid monomer composition of the first step and PEDOT:PSS as a conductive polymer and thermally polymerizing the acrylic acid monomer to form PAA (polyacrylic acid) which is a template polymer network, thereby primarily manufacturing the hydrogel (FIG. 4).

The third step is a step of inserting and heating the hydrogel having a template formed thereon in an organic solvent, separating PEDOT and PSS from the conductive polymer, removing the organic solvent and activating the connection between PEDOTs to form a hydrogel containing a double network. In this process, the large-sized PSS is separated from PEDOT:PSS, the separated PSS is prevented from obstructing the electrical connection path, and PEDOT can grow along the template network to form a uniform network.

That is, the method includes a step of separating PEDOT and PSS from PEDOT:PSS contained in a hydrogel having a matrix including polyacrylic acid and PEDOT:PSS formed through polymerization using an organic solvent.

The organic solvent for separating PEDOT and PSS from the PEDOT:PSS can be selected from polar solvents having a large dipole moment. According to one embodiment of the invention, the organic solvent may be one or more selected from the group consisting of dimethyl sulfoxide (DMSO), ethylene glycol, glycerol, and N,N-dimethylacetamide. More specifically, the organic solvent may be dimethyl sulfoxide.

In the synthesis of the hydrogel of a preferred embodiment of the invention, the third step is a process in which PEDOT and PSS are separated by adding DMSO, which is a solvent that can interact with PSS, while PEDOT and PSS are adhered through ionic interaction. In addition, the entire solvent can be dried by heating at 95° C. to blow off all the solvent, thereby activating connection between PEDOTs.

The thermal polymerization can be performed at 75 to 85° C. for 2 to 4 hours.

The heating can be performed at 95 to 100° C. for 16 to 24 hours.

The conductive polymer of the third step can be formed uniformly and thinly along the network containing polyacrylic acid, thereby forming a network containing three-dimensional nanofibers. That is, in the conductive polymer of the third step, PEDOT and PSS are separated along a network containing polyacrylic acid, and each can form a network.

The present invention may further comprise a step of immersing the produced hydrogel in water after the third step in order to maintain the state of the produced hydrogel.

That is, after the third step, the method may further comprise a step of immersing a film having three-dimensional nanofibers formed thereon in water again and hydrating the film to form a hydrogel having a uniform network.

This process makes it possible to provide a highly conductive tissue-like hydrogel adhesive having the above-described characteristics.

In this manner, the hydrogel has PEDOT polymers with high electrical conductivity connected to each other in a three-dimensional structure, and can exhibit the highest electrical conductivity among the reported conductive polymer hydrogels. In addition, the hydrogel shows very high ionic conductivity and low impedance because PEDOT and PSS form a thin nanofiber three-dimensional structure.

Furthermore, in biosystems, ions rather than electrons transmit signals, and the ionic conductivity of bioelectronic elements is important. Thus, the hydrogel has high ionic conductivity and is therefore very suitable as a bioelectrode. Further, because the hydrogel is a double structure hydrogel of PAA and PEDOT:PSS, it is soft, stretches easily, exhibits high toughness, and has strong properties against compression. In addition, the hydrogel can safely maintain excellent adhesion for a long period of time without inflammatory effects when applied to biological tissues.

Therefore, the hydrogel according to the present invention can simultaneously ensure very high electrical conductivity, good stretchable property, and soft physical properties, and is stable, and thus it can be effectively used when applied to biological tissues.

Below, preferred examples of the invention, comparative examples, and experimental examples for evaluating them will be described. However, the following example is only a preferred example of the invention, and the present invention is not limited by the following example.

EXAMPLES AND COMPARATIVE EXAMPLES: PREPARATION OF HYDROGEL

Example 1

A hydrogel was prepared by the method shown in FIG. 4.

First, 100 parts by weight (8 mmol) of acrylic acid monomer, and ammonium persulfate and N,N-methylenebisacrylamide were added at 0.95 parts by weight (0.35 mol % in terms of moles) and 0.75 parts by weight (0.3 mol % in terms of moles) relative to the monomer, and mixed with 2.5 mL of deionized water to prepare an acrylic monomer composition (step 1).

Subsequently, the solution prepared above was mixed with 9.1 parts by weight (5.2 mL) of the PEDOT:PSS solution relative to 100 parts by weight of the acrylic acid monomer to ensure that all particles were well dissolved.

The solution prepared above was degassed, and thermally polymerized at 75° C. for 2 hours to prepare a template polymer network, thereby initially producing a hydrogel (step 2).

Then, the hydrogel was immersed in 2.5 mL of dimethyl sulfoxide (DMSO) solution, and heated at 95° C. for 18 hours to create a PEDOT network, and PEDOT and PSS were separated and dispersed in polyacrylic acid to prepare a polymer that formed a three-dimensional nanofiber (step 3).

Then, the polymer was again inserted and immersed in water to form the final hydrogel state (hydrogel containing PEDOT and PSS networks dispersed in PAA and PAA) (step 4).

Comparative Example 1

This is a method of making a common PEDOT:PSS hydrogel. 1.3 mL of DMSO was mixed with 10 mL of PEDOT:PSS aqueous solution, and all the solvent was blown off at a temperature of 95° C. for 18 hours to form a film, which was then hydrated in water again to prepare PEDOT:PSS-based hydrogel.

Comparative Example 2

0.1 g of polyaniline (PANI) and 1 g of each of water-soluble polymers (polyacrylic acid, polyacrylamide, polyethylene glycol) were mixed with 2.5 mL of water. After curing, DMSO was added thereto, and heated at 95° C. for 18 hours, and the solvent was blown off to form a film, which was then hydrated in water again to prepare a polyaniline (PANI)-based hydrogel.

Comparative Example 3

0.1 g of polypyrrole (PPy) and 1 g of each of water-soluble polymers (polyacrylic acid, polyacrylamide, and polyethylene glycol) were mixed, and DMSO was added thereto, and the mixture was heated at 95° C. for 18 hours. Then, the solvent was blown off to form a film, which was again hydrated in water. Thereby, polypyrrole (PPy)-based hydrogel was prepared.

Comparative Example 4

0.5 g of silver flake or 0.5 g of silver nanowire and 4 g of polyacrylamide were mixed to make a metal-based conductive hydrogel. Thereby, a metallic hydrogel without using a conductive polymer was prepared.

Comparative Example 5

As a hydrogel in which no PEDOT:PSS fiber network was formed within polyacrylic acid, a low-conductivity PEDOT:PSS hydrogel was prepared in the same manner as in Example 1, except for the third and final steps in Example 1 using heating of the solvent and water.

Comparative Example 6

In Example 1, an aqueous solution prepared by mixing acrylic acid monomer, initiator, and curing agent without using a conductive polymer was thermally polymerized to prepare a polyacrylic acid (PAA) hydrogel.

Comparative Example 7

As a hydrogel composed only of soft polyacrylic acid, polyacrylamide, and polyethylene glycol water-soluble polymers, a soft hydrogel was prepared by mixing 1 g each of polyacrylic acid, polyacrylamide, and polyethylene glycol in 10 mL water and polymerizing the water-soluble polymer without PEDOT:PSS.

Experimental Example

The physical properties of the hydrogels of Examples and Comparative Examples were evaluated by the following method, and the results are shown in FIGS. 5*a* to 16.

1. Comparison of Hydrogel Structures

The hydrogel structure was confirmed using an atomic force microscope (AFM) device.

Figure 5A:
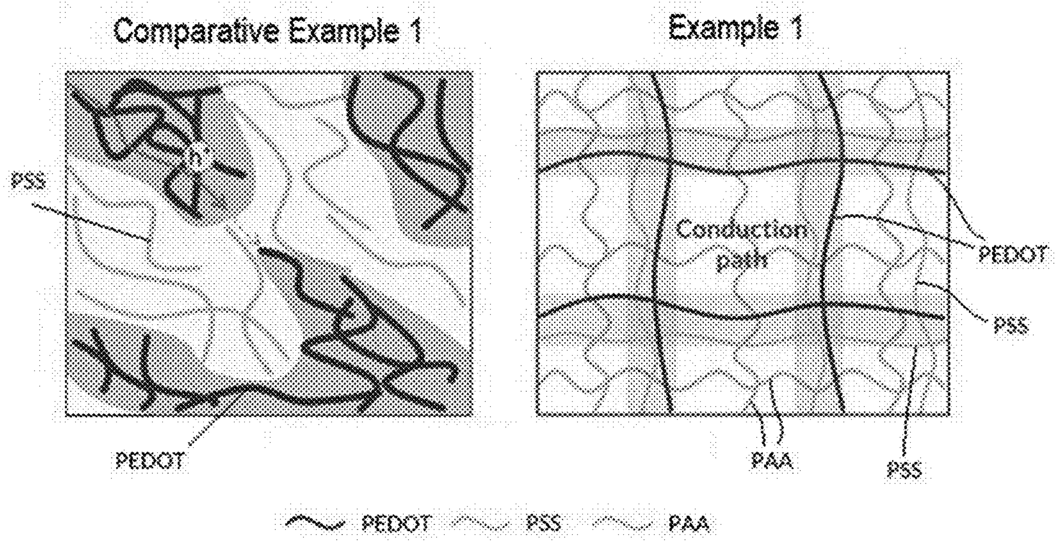
FIG. 5*a* is a comparative schematic diagram of the hydrogel structure composed of the existing PEDOT:PSS of Comparative Example 1 and the hydrogel structure composed of polyacrylic acid and PEDOT:PSS of Example 1.

FIG. 5*a* is a comparative schematic diagram of the hydrogel structure composed of the existing PEDOT:PSS of Comparative Example 1 and the hydrogel structure composed of polyacrylic acid and PEDOT:PSS of Example 1.

Figure 5B:
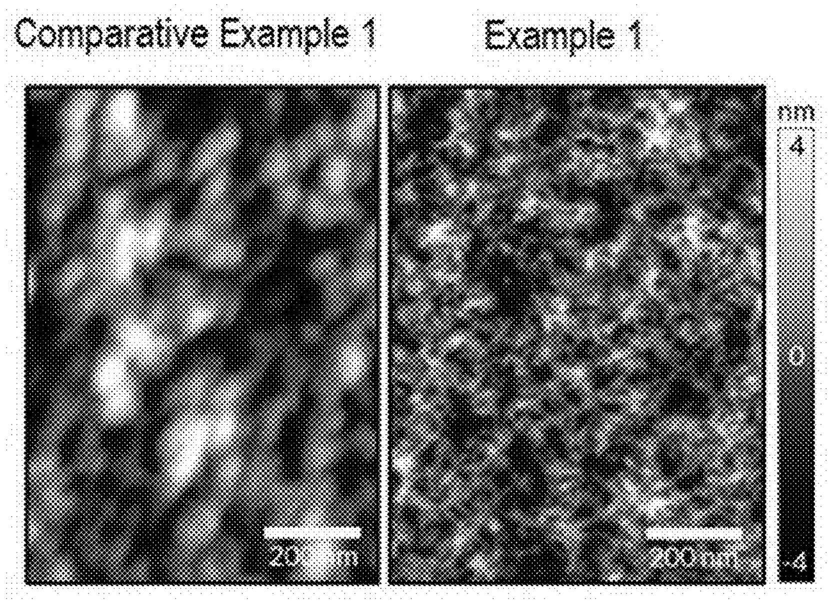
FIG. 5*b* shows a comparison of AFM height (atomic force microscopy height) images of Comparative Example 1 and Example 1.

FIG. 5*b* shows a comparison of AFM height (atomic force microscopy height) images of Comparative Example 1 and Example 1.

As shown in FIGS. 5*a* and 5*b*, Example 1 of the present invention exhibited a very high electrical conductivity of 247 S/cm in a form in which all large-sized PSS domains were removed. Therefore, it can be confirmed that PEDOT polymers with high electrical conductivity are connected to each other in a three-dimensional structure, and thus exhibit the highest electrical conductivity among the reported conductive polymer hydrogels.

On the other hand, in the hydrogel of Comparative Example 1, in which only general conductive polymers according to previous research were used, PSS grew greatly and disturbed the connection between PEDOTs, resulting in a decrease in electrical conductivity.

2. Evaluation of Adhesive Property of Hydrogel

After adhering the hydrogel (sample size: 1 cm×4 cm) to biological tissue (1.5 cm×7 cm), the interface toughness was measured immediately after adhesion of the hydrogel and after 2 weeks of adhesion.

The interface toughness was measured by adhering the hydrogel to the biological tissue and then peeling off the hydrogel from the biological tissue at an angle of 1800 using a universal tensile tester.

Figure 6A:
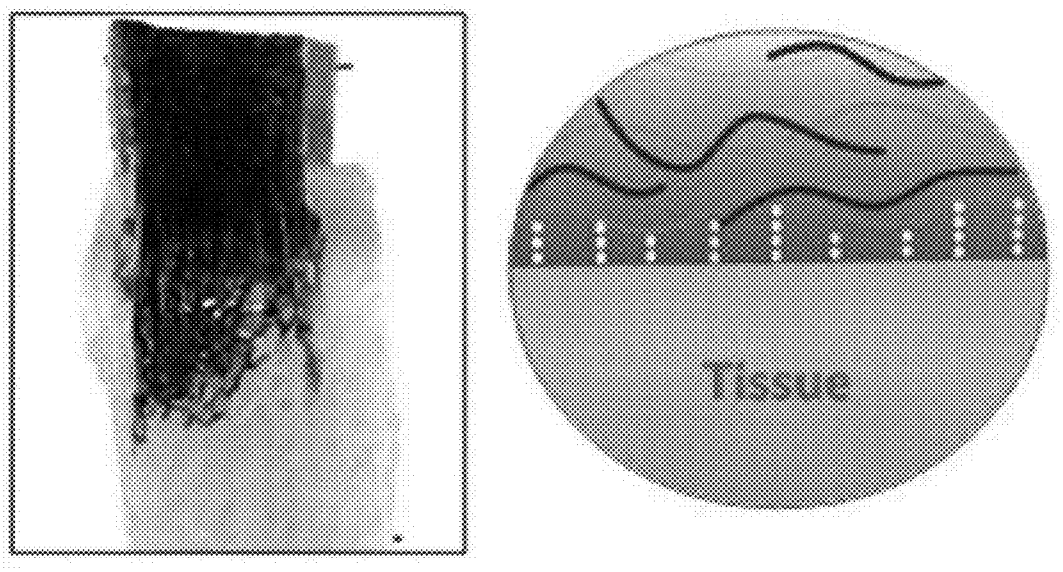
FIG. 6*a* briefly shows the interface adhesion between biological tissues and tissues when the hydrogel of Example 1 is adhered to biological tissues.
Figure 6B:
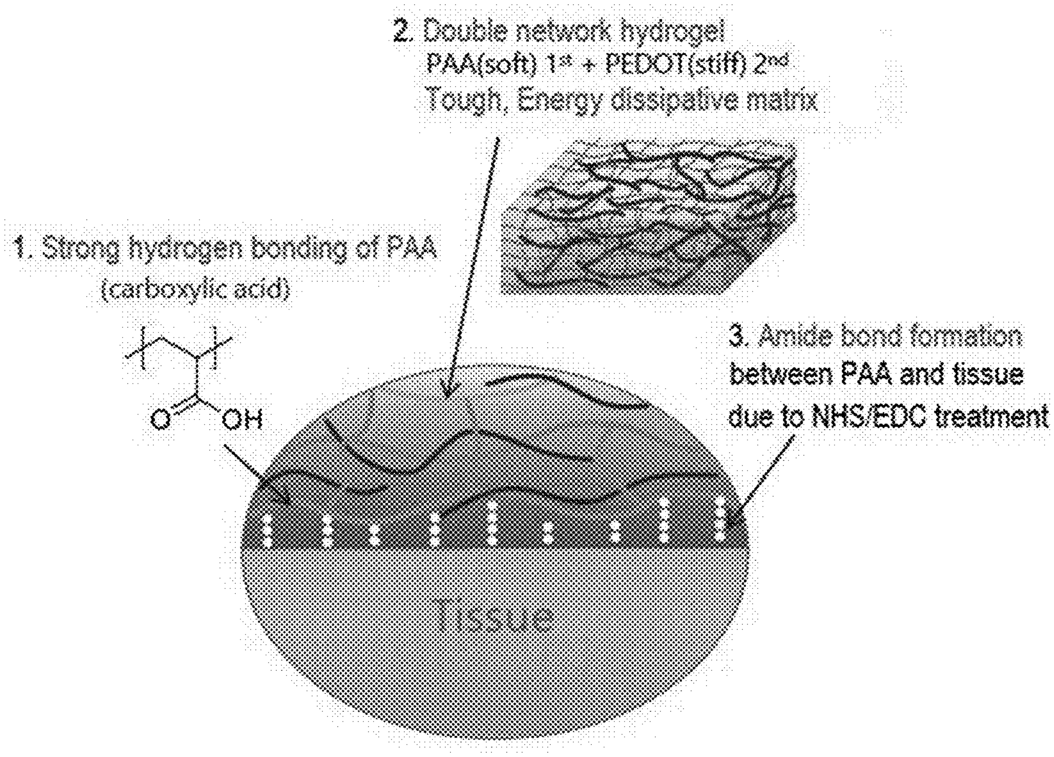
FIG. 6*b* shows the adhesion principle at the adhesive interface between the biological tissue and the hydrogel in FIG. 6*a*.
Figure 6C:
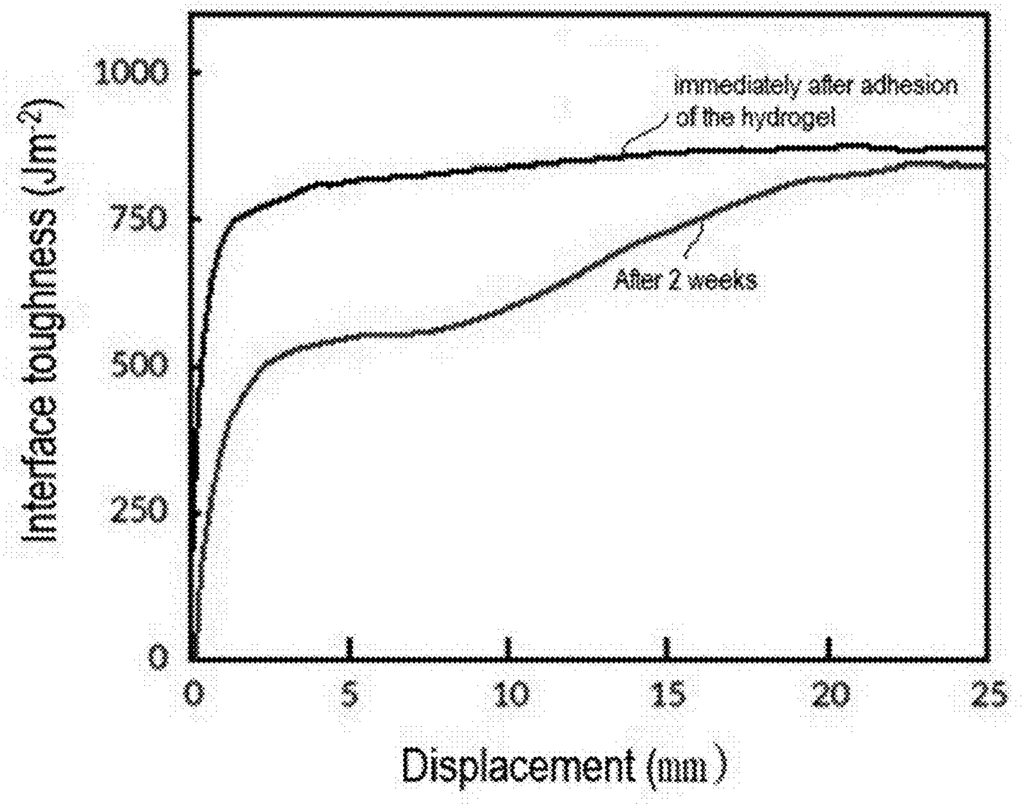
FIG. 6*c* is a graph showing the skin adhesion of the hydrogel of Example 1 over time.

FIG. 6*a* briefly shows the interface adhesion between biological tissues and tissues when the hydrogel of Example 1 is adhered to biological tissues. FIG. 6*b* shows the adhesion principle at the adhesive interface between the biological tissue and the hydrogel in FIG. 6*a*. FIG. 6*c* is a graph showing the skin adhesion of the hydrogel of Example 1 after two weeks.

Looking at FIGS. 6*a* to 6*b*, the hydrogel of Example 1 was made of PAA, which can form a strong hydrogen bond with the skin, and also had a double structure, so it had excellent energy dissipation ability and exhibited strong adhesion to the skin.

In addition, in order to properly sense biological signals and effectively provide biological stimulation, the biological tissue and the device must be strongly adhered and not fall off even if external force is applied.

Therefore, by spraying a catalyst solution (NHS, EDC) on the interface to further form a covalent bond at such a bonding portion, it has very high adhesion energy and can be stably adhered to the skin.

Similar to FIG. 6*c*, the hydrogel of Example 1 had excellent adhesion properties between the living tissue and the adhesive interface even after 2 weeks of adhesion to the biological tissue, and was stably adhered to the skin.

3. Evaluation of Electrical Conductivity of Hydrogels

The electrical conductivity of the hydrogel was measured by a method of measuring sheet resistance using 4-point probe, a current source, and a voltmeter.

Figure 7:
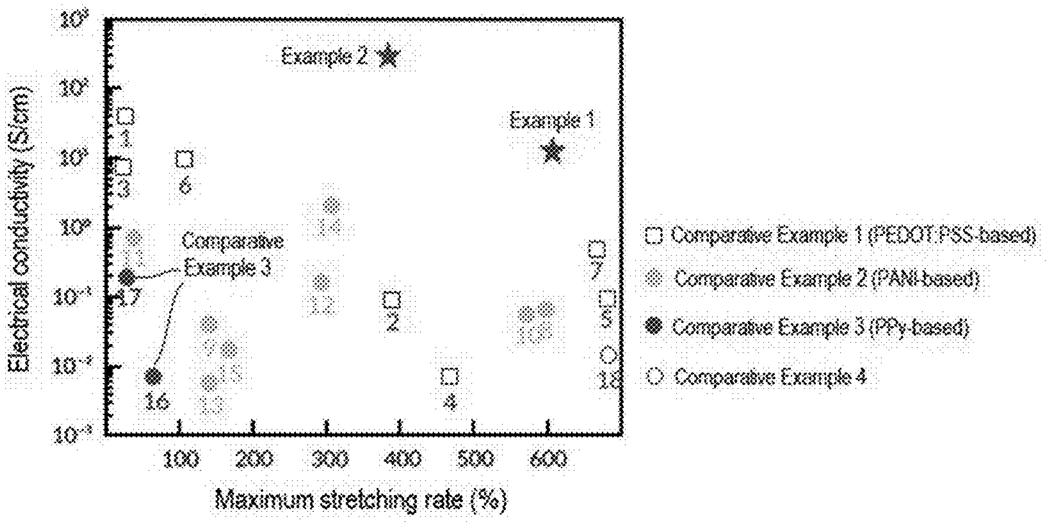
FIG. 7 shows a comparison of the electrical conductivity by the change in maximum stretching rate of Examples 1 and 2 and Comparative Examples 1 to 4.

FIG. 7 shows a comparison of the electrical conductivity by the change in maximum stretching rate of Examples 1 and 2 and Comparative Examples 1 to 4.

As shown in FIG. 7, it was confirmed that the hydrogel of Example 1 exhibited the highest electrical conductivity among the reported conductive polymer hydrogels because PEDOT polymers with higher electrical conductivity than Comparative Examples 1 to 4 are connected to each other in a three-dimensional structure.

4. Measurement of Impedance of Hydrogel

The impedance of the hydrogel was measured under a three-electrode system using the hydrogel as a working electrode, Pt wire as a counter electrode, and Ag/AgCl as a reference electrode in phosphate buffered saline (PBS).

Figure 8:
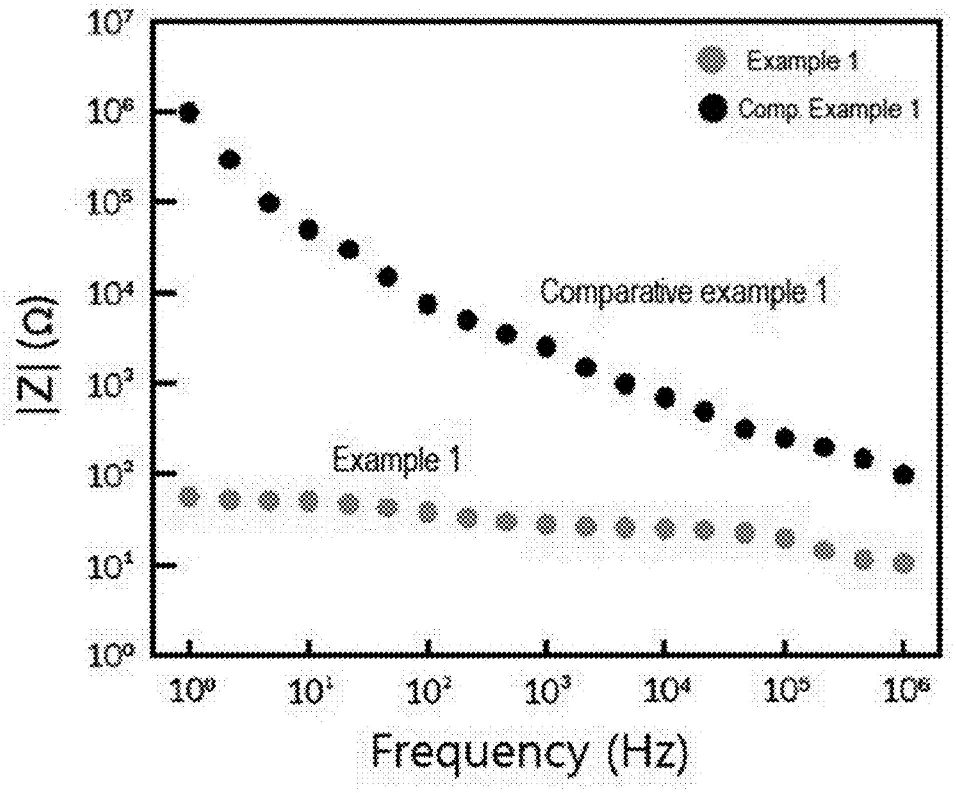
FIG. 8 shows impedance graphs of Example 1 and Comparative Example 1.

FIG. 8 shows impedance graphs of Example 1 and Comparative Example 1.

In addition, Example 1 has very high ionic conductivity and exhibits low impedance because PEDOT and PSS form a thinner nanofiber three-dimensional structure that in Comparative Example 1 (PEDOT:PSS-based hydrogel (FIG. 8). In biosystems, ions rather than electrons transmit signals, and thus the ionic conductivity of bioelectronic devices is important. Therefore, this hydrogel has high ionic conductivity and is very suitable as a bioelectrode.

5. Evaluation of Mechanical Properties of Hydrogel

The tensile strength and toughness of the hydrogel were measured by a method of measuring the force while pulling the hydrogel with a universal tensile tester.

Figure 9A:
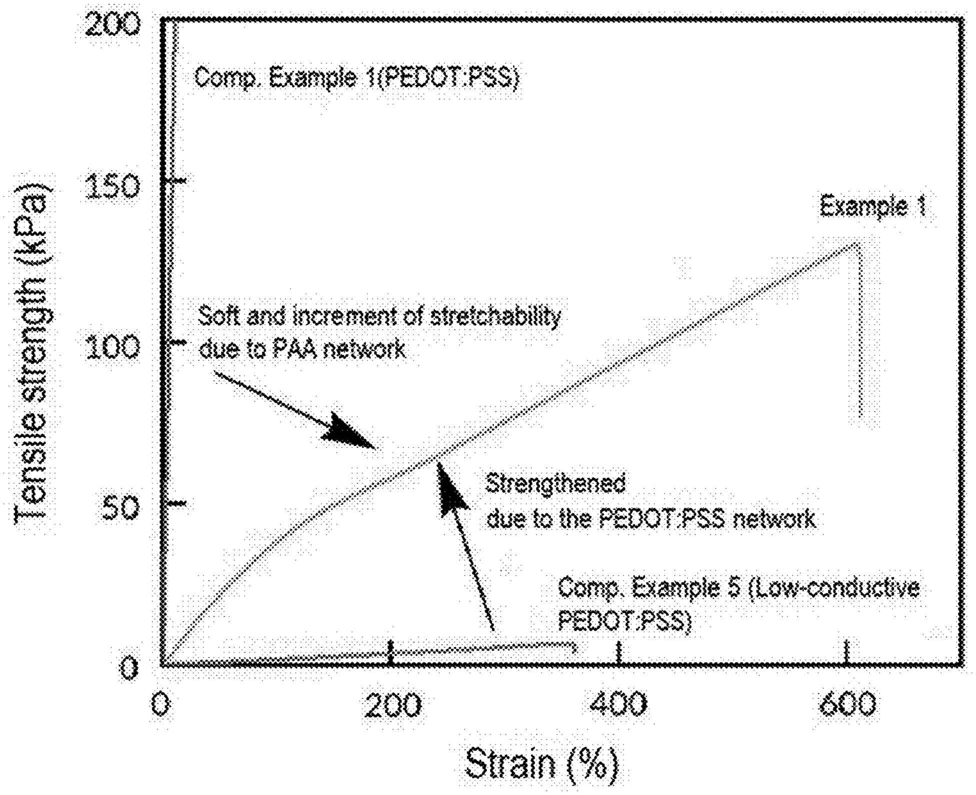
FIG. 9*a* shows a comparison of the mechanical properties (tensile strength) of Example 1, Comparative Example 1, and Comparative Example 5.
Figure 9B:
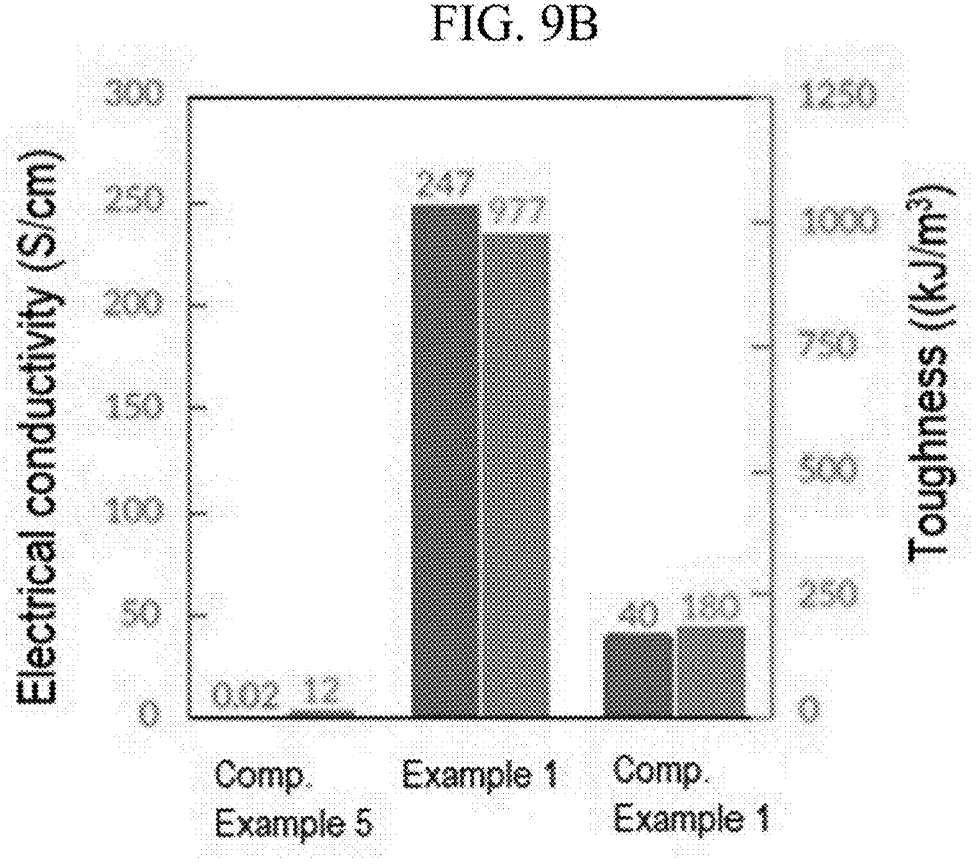
FIG. 9*b* is a comparison graph of the electrical conductivity and toughness of Example 1, Comparative Example 1 (PEDOT:PSS), and Comparative Example 5 (low conductivity PEDOT:PSS hydrogel).

FIG. 9*a* shows a comparison of the mechanical properties (tensile strength) of Example 1, Comparative Example 1, and Comparative Example 5. FIG. 9*b* is a comparison graph of the electrical conductivity and toughness of Example 1, Comparative Example 1 (PEDOT:PSS), and Comparative Example 5 (low conductivity PEDOT:PSS hydrogel).

In addition, because the hydrogel of Example 1 was a hydrogen with a double structure of PAA and PEDOT:PSS, it was soft, stretched more easily, and exhibited high toughness (FIGS. 9*a* and 9*b*). Therefore, it can be confirmed that Example 1 had better mechanical properties than Comparative Example 1, and is also better in both electrical conductivity and toughness.

6. Measurement of Compressibility of Hydrogel

The compressibility of the hydrogel was measured by a method of compressing the hydrogel with a universal tensile tester.

Figure 10:
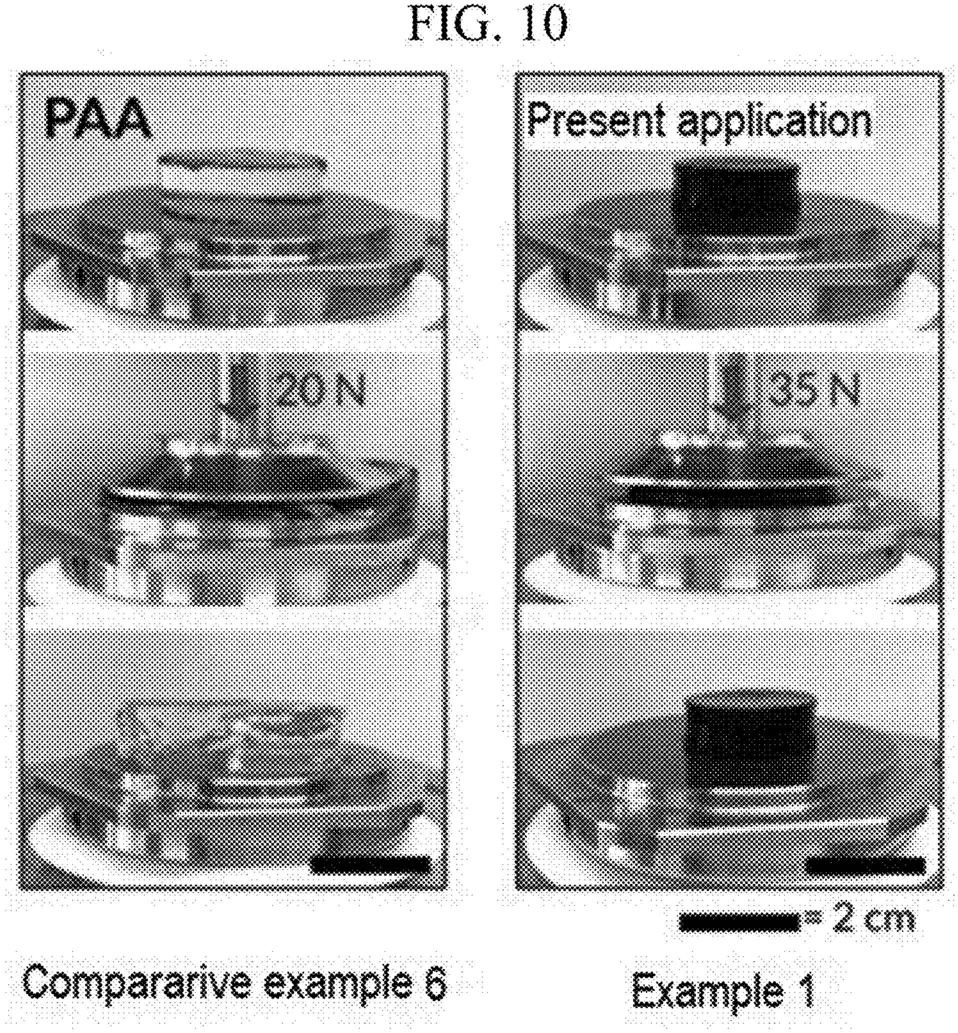
FIG. 10 is photographs comparing the compression of the hydrogels of Example 1 and Comparative Example 6 (PAA).

FIG. 10 is photographs comparing the compression of the hydrogels of Example 1 and Comparative Example 6 (PAA).

When comparing the compression of the hydrogels of Example 1 and Comparative Example 6, Comparative Example 6 showed that the shape was deformed and collapsed under conditions of compression with a load of 20N, but Example 1 showed that its shape was maintained excellently even when compressed with a load of 35N. Therefore, the hydrogel of Example 1 has strong properties even when compressed (FIG. 10).

7. Measurement of Modulus of Hydrogel

The modulus of the hydrogel was measured by stretching the hydrogel using a universal tensile tester and determining the slope of the initial strain-stress.

Figure 11:
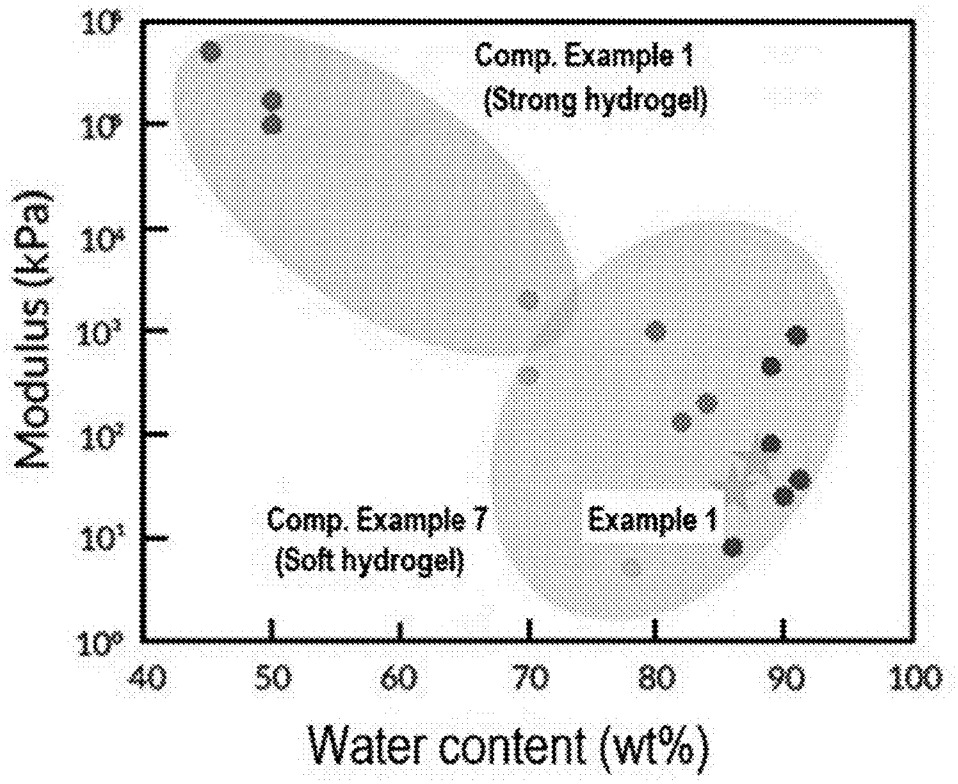
FIG. 11 is a graph comparing the modulus according to water content of Example 1, Comparative Example 1 (PEDOT:PSS), and Comparative Example 7 (soft hydrogel).

FIG. 11 is a graph comparing the modulus according to water content of Example 1, Comparative Example 1 (PEDOT:PSS), and Comparative Example 7 (soft hydrogel).

In FIG. 11, the hydrogel of Example 1 showed a good level of modulus compared to the strong or soft hydrogels of Comparative Example 1 and Comparative Example 7 even under water content conditions of 80 wt. % or more.

8. Evaluation of Electrode Resistance of Hydrogel

Electrode resistance due to the stretching of the hydrogel was measured by a method of adhering the hydrogel to a stretching machine that constantly pulls it and then measuring the resistance at both ends of the hydrogel.

Figure 12:
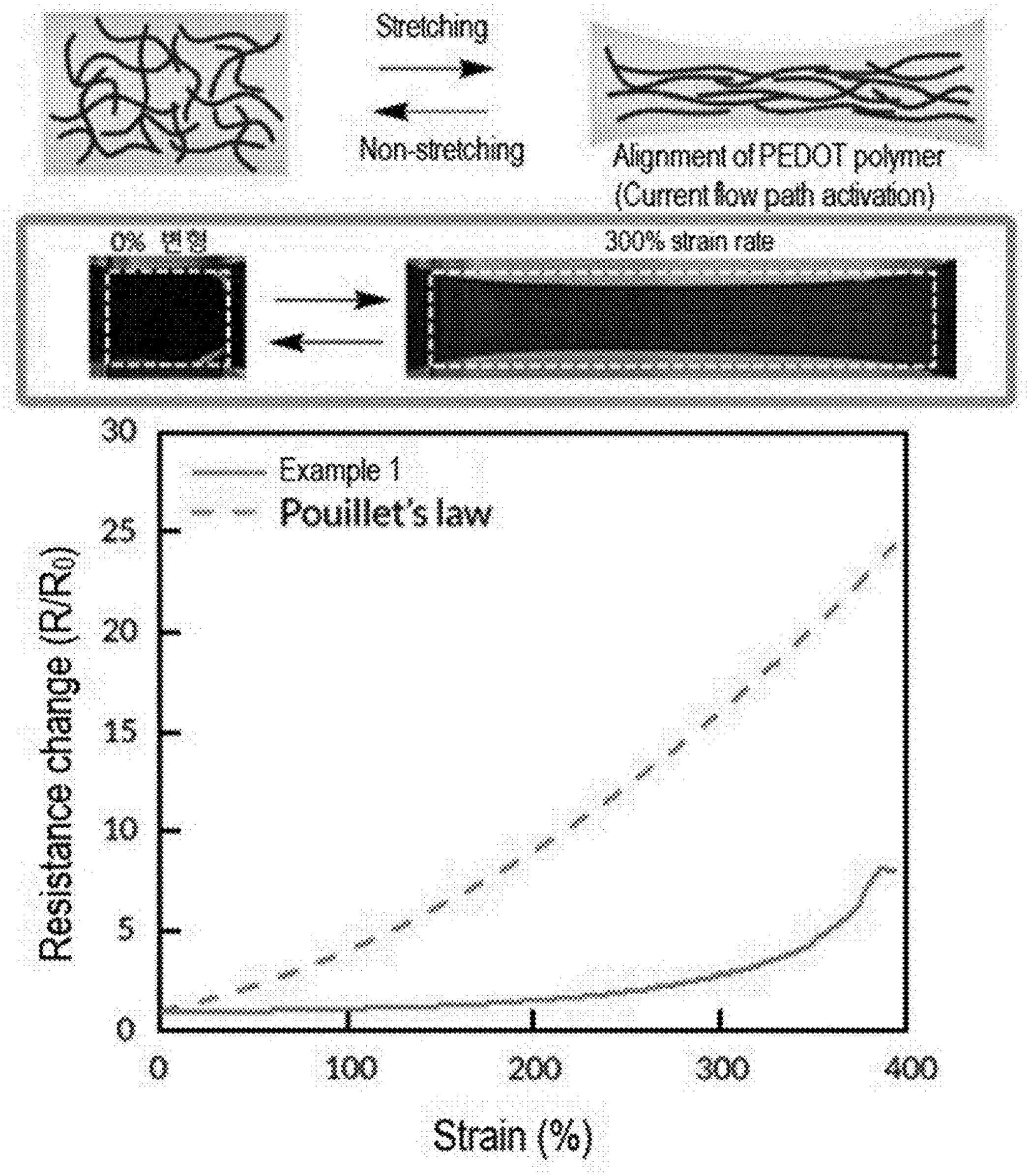
FIG. 12 is a graph of resistance change due to stretching in Example 1 (comparison based on Pouillet's Law).
Figure 13:
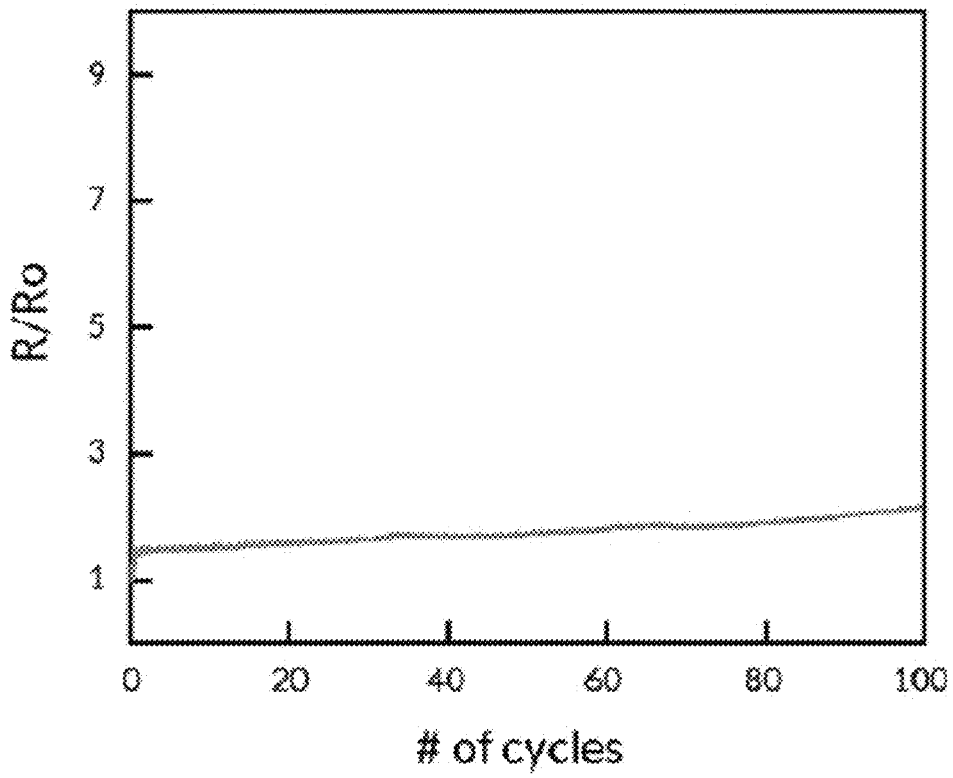
FIG. 13 is a graph of resistance change due to stretching 100 times in Example 1.

FIG. 12 is a graph of resistance change due to stretching in Example 1 (comparison based on Pouillet's Law). FIG. 13 is a graph of resistance change due to stretching 100 times in Example 1.

Moreover, in order to stably operate a biological tissue device that moves frequently, it is important that the resistance of the electrode does not change even when stretched. It can be seen that the hydrogel of Example 1 hardly changes in resistance even when the conductive network is well-connected, the polymer, which was randomly aligned when stretched, align in one direction and is stretched (FIG. 12). In addition, it can be seen that Example 1 hardly changed in resistance even after being stretched 100 times, and the electrical properties were restored to their original state (FIG. 13).

9. Measurement of Physical Properties of Hydrogel in Bioelectronic Device Electrodes A device made of two hydrogel electrodes was adhered to the sciatic nerve of an anesthetized rat, and a potential difference was applied between the electrodes to measure the movement of the legs in response to the voltage. An electrocardiogram signal test was performed by adhering a device consisting of two hydrogel electrodes to the heart of an anesthetized rat and measuring the electrocardiogram coming from the heart.

Figure 14:
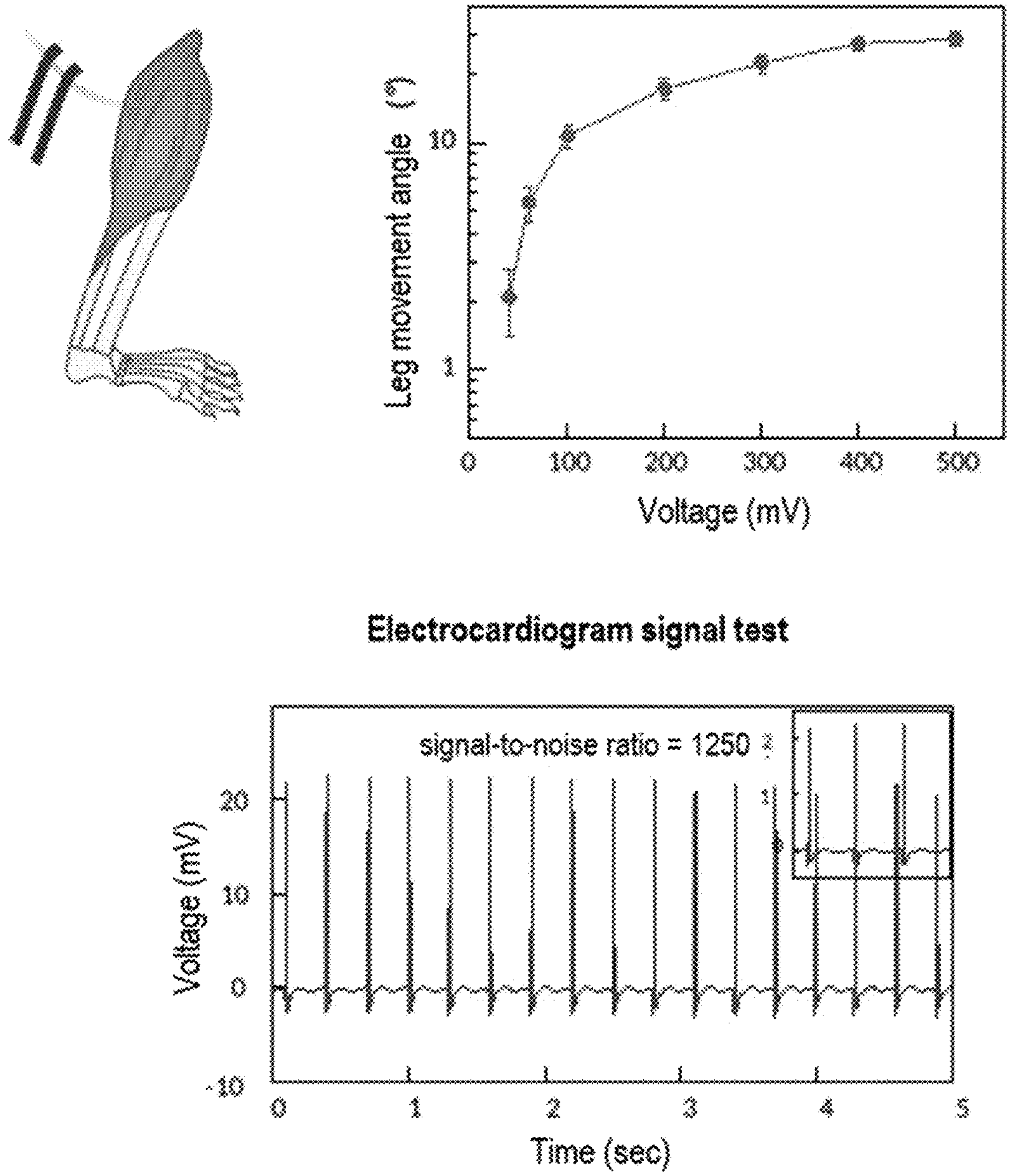
FIG. 14 is a diagram showing voltage by leg movement and electrocardiogram signal test results when applied as a bioelectronic device electrode of Example 1.

FIG. 14 is a diagram showing voltage by leg movement and electrocardiogram signal test results when applied as a bioelectronic device electrode of Example 1.

In previous FIG. 6*c*, it was confirmed that the hydrogel of Example 1 was stably adhered to the skin even after 2 weeks.

Through this, it was possible to stimulate the sciatic nerve at a very low voltage (40 mV) when applying the hydrogel of Example 1 as a biological tissue device, as shown in FIG. 14. This voltage is the lowest value among the reported nerve stimulation voltages, confirming that this hydrogel can be operated at ultra-low voltage.

Further, a high signal-to-noise ratio of 1250 could be achieved when reading ECG signals. Previously, additional signal processing was required to obtain such a high signal-to-noise ratio. However, when using this hydrogel, it was possible to implement it with a very simple structure without such an operation.

10. Evaluation of Hydrogel Usability

The hydrogel was laser-patterned by burning the hydrogel with a laser marker so that the desired pattern appeared.

Figure 15:
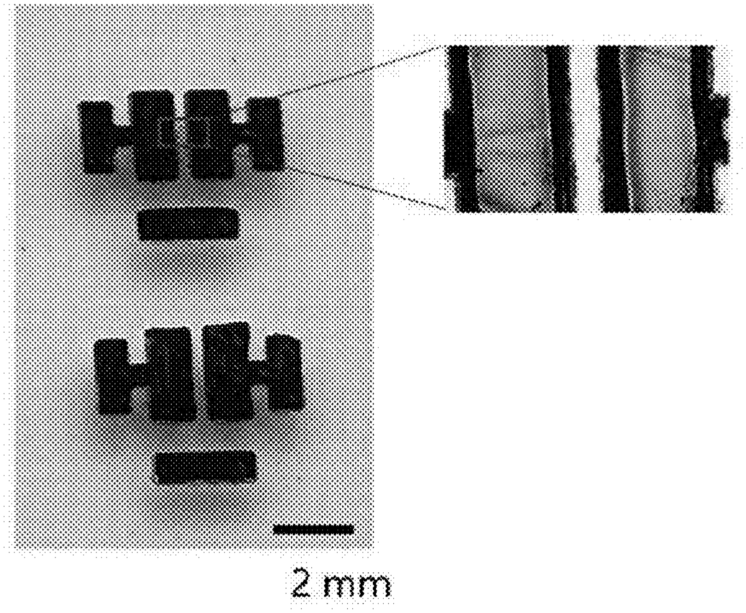
FIG. 15 is a photograph of laser patterning of the hydrogel of Example 1.
Figure 16:
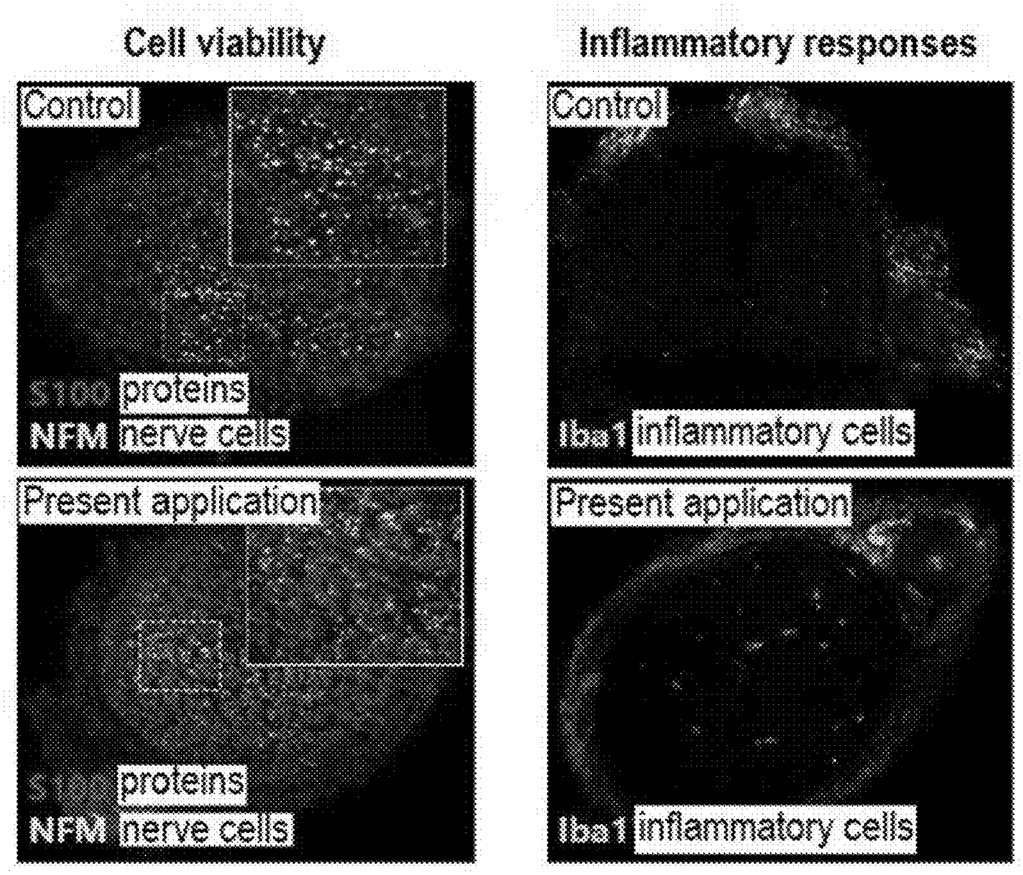
FIG. 16 is an immunohistochemical photograph measured after inserting the hydrogel of Example 1 in vivo for 2 weeks.

FIG. 15 is a photograph of laser patterning of the hydrogel of Example 1. FIG. 16 is an immunohistochemical photograph measured after inserting the hydrogel of Example 1 in vivo for 2 weeks.

As a result of laser patterning to increase its usability as a bio-interface electrode, it was confirmed that Example 1 is a patternable material that can be sufficiently used in bioelectronic devices such as electroencephalograms (FIG. 15).

In addition, the hydrogel of Example 1 was adhered to the sciatic nerve of a rat for 2 weeks, and cell viability and inflammatory response of the hydrogel were evaluated using immunohistochemical staining.

To be used as a bio-interface electrode, biocompatibility is important. However, as shown in FIG. 16, all were made of biocompatible materials, so even when the hydrogel of Example 1 was inserted into the body for two weeks, no inflammatory response occurred, and no adverse reactions of cells were observed.

The invention claimed is:

1. A highly conductive hydrogel adhesive in which:

a three-dimensional nanofiber containing a PEDOT network and a PSS network are formed along polyacrylic acid within a matrix containing polyacrylic acid, the three-dimensional nanofiber is formed by heating a hydrogel formed through polymerization of an acrylic acid monomer containing an organic solvent and PEDOT:PSS, which is a conductive polymer, so that PEDOT and PSS are separated and dispersed from the conductive polymer, and 4.8 to 9.1 parts by weight of the conductive polymer in the hydrogel is crosslinked with respect to 100 parts by weight of polyacrylic acid, wherein the hydrogel has an electrical conductivity of 200 S/cm or more, a maximum stretching rate of 400 to 600%, an impedance of 28Ω at 1 KHz, a tensile strength of 120 to 350 kPa and a resistance storage capacity of 31 to 80 mC/cm2.

2. The highly conductive hydrogel adhesive as claimed in claim 1, wherein:

the organic solvent is one or more selected from the group consisting of dimethyl sulfoxide, ethylene glycol, glycerol, and N,N-dimethylacetamide.

3. The highly conductive hydrogel adhesive as claimed in claim 1, wherein:

the nanofiber further comprises a hydrophilic polymer.

4. The highly conductive hydrogel adhesive as claimed in claim 1, wherein:

the polyacrylic acid of the matrix has a weight average molecular weight of 100,000 to 150,000 g/mol.

5. The highly conductive hydrogel adhesive as claimed in claim 1, wherein:

the hydrogel further comprises water.

6. A method of manufacturing a highly conductive hydrogel adhesive, the method comprising:

a first step of adding an acrylic acid monomer, a polymerization initiator, and a crosslinking agent to a water-soluble solvent to prepare an acrylic acid monomer composition;

a second step of adding PEDOT:PSS as a conductive polymer to the acrylic acid monomer composition and thermally polymerizing the acrylic acid monomer to produce a hydrogel that formed a network containing polyacrylic acid as a matrix polymer; and a third step of heating the hydrogel that formed a network containing polyacrylic acid in an organic solvent to blow off all the solvent, thereby manufacturing a film containing three-dimensional nanofibers in which conductive polymers are formed uniformly and thinly along polyacrylic acid, which is a matrix polymer, wherein the conductive polymer in the third step separates PEDOT and PSS along a network containing polyacrylic acid to form a network, respectively, and wherein the conductive polymer is contained in an amount of 4.8 to 9.1 parts by weight with respect to 100 parts by weight of the acrylic acid monomer wherein the hydrogel has an electrical conductivity of 200 S/cm or more, a maximum stretching rate of 400 to 600%, an impedance of 280 at 1 KHz, a tensile strength of 120 to 350 kPa and a resistance storage capacity of 31 to 80 mC/cm2.

7. The method of manufacturing a highly conductive tissue-like hydrogel adhesive as claimed in claim 6, wherein the acrylic acid monomer composition includes 0.95 to 2 parts by weight of a polymerization initiator and 0.75 to 1.5 parts by weight of a hydrophilic polymer with respect to 100 parts by weight of the acrylic acid monomer.

8. The method of manufacturing a highly conductive tissue-like hydrogel adhesive as claimed in claim 6, wherein after the third step, the method further comprises a fourth step of immersing a film having three-dimensional nanofibers formed thereon in water again and hydrating the film to form a hydrogel having a uniform network.

9. The method of manufacturing a highly conductive tissue-like hydrogel adhesive as claimed in claim 6, wherein the thermal polymerization is performed at 75 to 85° C. for 2 to 4 hours.

10. The method of manufacturing a highly conductive tissue-like hydrogel adhesive as claimed in claim 6, wherein the organic solvent is one or more selected from the group consisting of dimethyl sulfoxide, ethylene glycol, glycerol, and N, N-dimethylacetamide.

11. The method of manufacturing a highly conductive tissue-like hydrogel adhesive as claimed in claim 6, wherein the heating is performed at 95 to 100° C. for 16 to 24 hours.

* * * * *